(12) United States Patent
Sambu et al.

(10) Patent No.: US 7,481,647 B2
(45) Date of Patent: Jan. 27, 2009

(54) SYSTEMS AND METHODS FOR FABRICATING 3-D OBJECTS

(75) Inventors: Shiva P. Sambu, Mountain View, CA (US); Long Phan, Santa Clara, CA (US); Srinivas Kaza, San Francisco, CA (US); Michael J. Doung, El Cerrito, CA (US)

(73) Assignee: Align Technology, Inc., Santa Clara, CA (US)

( * ) Notice: Subject to any disclaimer, the term of this patent is extended or adjusted under 35 U.S.C. 154(b) by 925 days.

(21) Appl. No.: 10/867,099

(22) Filed: Jun. 14, 2004

(65) Prior Publication Data

US 2005/0275129 A1    Dec. 15, 2005

(51) Int. Cl.
*B28B 5/00* (2006.01)
(52) U.S. Cl. .................... 425/436 R; 425/174.4; 425/375; 264/308; 264/401; 264/497; 264/113
(58) Field of Classification Search ............. 425/436 R, 425/556, 375, 174.4; 264/308, 401, 497, 264/113
See application file for complete search history.

(56) References Cited

U.S. PATENT DOCUMENTS

| | | | |
|---|---|---|---|
| 3,671,159 A * | 6/1972 | Greenberg et al. ........... 425/155 |
| 3,893,644 A * | 7/1975 | Drazick ........................ 249/68 |
| 4,050,666 A * | 9/1977 | Van Tichelt ................... 249/68 |
| 4,575,330 A | 3/1986 | Hull |
| 5,429,492 A * | 7/1995 | Taniyama .................... 425/556 |
| 5,468,141 A * | 11/1995 | Iwami et al. ................. 425/542 |
| 5,885,511 A | 3/1999 | Heller et al. |
| 5,975,893 A | 11/1999 | Chishti et al. |
| 6,183,248 B1 | 2/2001 | Chishti et al. |
| 6,187,247 B1 * | 2/2001 | Buzzell et al. ............... 264/334 |
| 6,210,162 B1 | 4/2001 | Chishti et al. |
| 6,217,325 B1 | 4/2001 | Chishti et al. |
| 6,227,850 B1 | 5/2001 | Chishti et al. |
| 6,227,851 B1 | 5/2001 | Chishti et al. |
| 6,299,440 B1 | 10/2001 | Phan et al. |
| 6,309,215 B1 | 10/2001 | Phan et al. |
| 6,318,994 B1 | 11/2001 | Chishti et al. |
| 6,371,761 B1 | 4/2002 | Cheang et al. |
| 6,386,864 B1 | 5/2002 | Kuo |
| 6,386,878 B1 | 5/2002 | Pavlovskaia et al. |

(Continued)

OTHER PUBLICATIONS

Solid Concepts Rapid Product Development—28231 Avenue Crocker, Bldg. 10, Valencia, CA 91355, *SLA Prototypes*, Website: http://www.solidconcepts.com/slapprototypes.html—SLA Prototypes, 2 pgs. Feb. 20, 2004.

*Primary Examiner*—Yogendra Gupta
*Assistant Examiner*—Maria Veronica D Ewald
(74) *Attorney, Agent, or Firm*—Klein, O'Neill & Singh, LLP

(57) ABSTRACT

Systems and methods are disclosed for a platform to form a three-dimensional article from successively selectively solidified layers of a liquid medium which is solidifiable by application thereto of a prescribed energy. The platform can be coated or uncoated. The platform can have an array of openings therethrough. Upon completion, the article can be removed from the platform using a punch having a plurality of projections adapted to engage openings in the platform. Alternatively, a tool can be used to push articles from the platform.

19 Claims, 9 Drawing Sheets

U.S. PATENT DOCUMENTS

| | | | |
|---|---|---|---|
| 6,390,812 B1 | 5/2002 | Chishti et al. |
| 6,394,801 B2 | 5/2002 | Chishti et al. |
| 6,398,548 B1 | 6/2002 | Muhammad et al. |
| 6,406,292 B1 | 6/2002 | Chishti et al. |
| 6,409,504 B1 | 6/2002 | Jones et al. |
| 6,450,807 B1 | 9/2002 | Chishti et al. |
| 6,454,565 B2 | 9/2002 | Phan et al. |
| 6,457,972 B1 | 10/2002 | Chishti et al. |
| 6,463,344 B1 | 10/2002 | Pavloskaia et al. |
| 6,471,511 B1 | 10/2002 | Chishti et al. |
| 6,485,298 B2 | 11/2002 | Chishti et al. |
| 6,488,499 B1 | 12/2002 | Miller |
| 6,497,574 B1 | 12/2002 | Miller |
| 6,499,997 B2 | 12/2002 | Chishti et al. |
| 6,514,074 B1 | 2/2003 | Chishti et al. |
| 6,524,101 B1 | 2/2003 | Phan et al. |
| 6,554,611 B2 | 4/2003 | Chishti et al. |
| 6,572,372 B1 | 6/2003 | Phan et al. |
| 6,582,227 B2 | 6/2003 | Phan et al. |
| 6,582,229 B1 | 6/2003 | Miller et al. |
| 6,602,070 B2 | 8/2003 | Miller et al. |
| 6,607,382 B1 | 8/2003 | Kuo et al. |
| 6,621,491 B1 | 9/2003 | Baumrind et al. |
| 6,626,666 B2 | 9/2003 | Chishti et al. |
| 6,629,840 B2 | 10/2003 | Chishti et al. |
| 6,633,789 B1 | 10/2003 | Nikolskiy et al. |
| 6,665,570 B2 | 12/2003 | Pavloskaia et al. |
| 6,682,346 B2 | 1/2004 | Chishti et al. |
| 6,685,469 B2 | 2/2004 | Chishti et al. |
| 6,685,470 B2 | 2/2004 | Chishti et al. |
| 6,688,886 B2 | 2/2004 | Hughes et al. |
| 6,699,037 B2 | 3/2004 | Chishti et al. |
| 6,705,861 B2 | 3/2004 | Chishti et al. |
| 6,705,863 B2 | 3/2004 | Phan et al. |
| 6,722,880 B2 | 4/2004 | Chishti et al. |
| 6,726,478 B1 | 4/2004 | Isiderio et al. |
| 6,729,876 B2 | 5/2004 | Chishti et al. |

\* cited by examiner

SYSTEMS AND METHODS FOR FABRICATING 3-D OBJECTS

BACKGROUND

This invention relates to a method of and apparatus for rapid forming of a solid three-dimensional article.

Stereolithography (SLA) prototypes are constructed from a liquid photopolymer that is selectively cured using an ultraviolet laser. The process begins with a 3D CAD file which is mathematically sliced into 2D cross sections. With the build apparatus positioned just below the surface of the photopolymer, a scanning system is used to draw the first cross section on the surface of the photopolymer, which adheres to the apparatus.

When the layer is complete, the elevator assembly lowers the apparatus into the vat and the next layer is drawn, with each new layer adhering to the previous one. The process repeats itself until the object is completed. Actual build times can range from under an hour to over a day, depending on the photopolymer, laser power, and the object geometry. Typically, a mechanical blade is used to sweep the surface of the photopolymer to ensure an even layer of resin for the next layer.

One supplier of SLA equipment is 3D Systems, Inc. of Valencia, Calif. Their system is discussed in U.S. Pat. No. 5,885,511. As discussed therein, the apparatus for forming a solid three-dimensional article from a liquid medium capable of solidification when subjected to prescribed energy are known in the prior art. For example, as discussed in the '511 patent, U.S. Pat. No. 4,575,330 to Charles W. Hull discloses a system for generating three-dimensional objects from a liquid medium by irradiating liquid layers with the aid of a computer programmed irradiation source and a translational mechanism.

Conventionally, each object fabricated requires grid-like structures that are attached to downfacing regions of the object (Supports). Supports provide a small, easy-to-remove, break-away region between the stereolithography apparatus (SLA) build apparatus and the object. The use of "sierras" in the construction of Supports minimizes the points of contact between the object and the supports themselves. Removing the supports from the part during Finishing is thereby made easier, and the surface finish of those regions where supports connect to the object, part or model are only minimally affected. If an object were built without supports, as the bottom-most layers of that object were cured by the SLA, solidified resin would become enmeshed in the openings of the SLA's apparatus. This condition would make it difficult-if not impossible-to remove finished parts without damaging them in the process. However, such sierras lengthen the object fabrication time. Moreover, removing the object is still labor intensive with the sierra approach.

SUMMARY OF THE INVENTION

Systems and methods are disclosed for a platform to form a three-dimensional article from successively selectively solidified layers of a liquid medium which is solidifiable by application thereto of a prescribed energy. The platform can be coated or uncoated. The platform can have an array of openings therethrough. Upon completion, the article can be removed from the platform using a punch having a plurality of projections adapted to engage openings in the platform. Alternative, a tool can be used to push articles from the platform.

In one aspect, an apparatus includes a platform having a plurality of openings therethrough; and a punch having a plurality of projections adapted to engage openings in the platform.

Implementations of the above aspect may include one or more of the following. The openings can be a regular array or can have an irregular pattern. The opening can be circular, oval, rectangular, tear-drop, triangular, elliptical or elongated in shape. The openings can be positioned on one or more columns. The platform can be Teflon material.

In another aspect, a method of forming a three-dimensional article from successively selectively solidified layers of a liquid medium which is solidifiable by application thereto of a prescribed energy includes placing an apparatus having a platform having a plurality of openings therethrough; forming the article in a body of said liquid medium held in a container, the article being formed above the apparatus; applying said prescribed energy to said fresh liquid medium in accordance with a defined pattern to selectively solidify said fresh liquid medium; and, repeating said coating and applying a plurality of times to form the article. After the article has been formed, a punch having a plurality of projections engages openings in the platform to eject the article from the platform. Alternatively, instead of a punch, a tool can be used to push the article from the platform.

Advantages of the invention may include one or more of the following. Object fabrication can be done without requiring support structures attached to downfacing regions of the object. The system allows removal of finished parts without damaging them in the process. The apparatus enables parts to be removed quickly without breakage. As a result, manufacturing speed is increased and manufacturing cost is decreased.

BRIEF DESCRIPTION OF THE DRAWINGS

A 3D fabrication apparatus incorporating the features of the invention is depicted in the attached drawings which form a portion of the disclosure and wherein.

DESCRIPTION

Figure 1A:
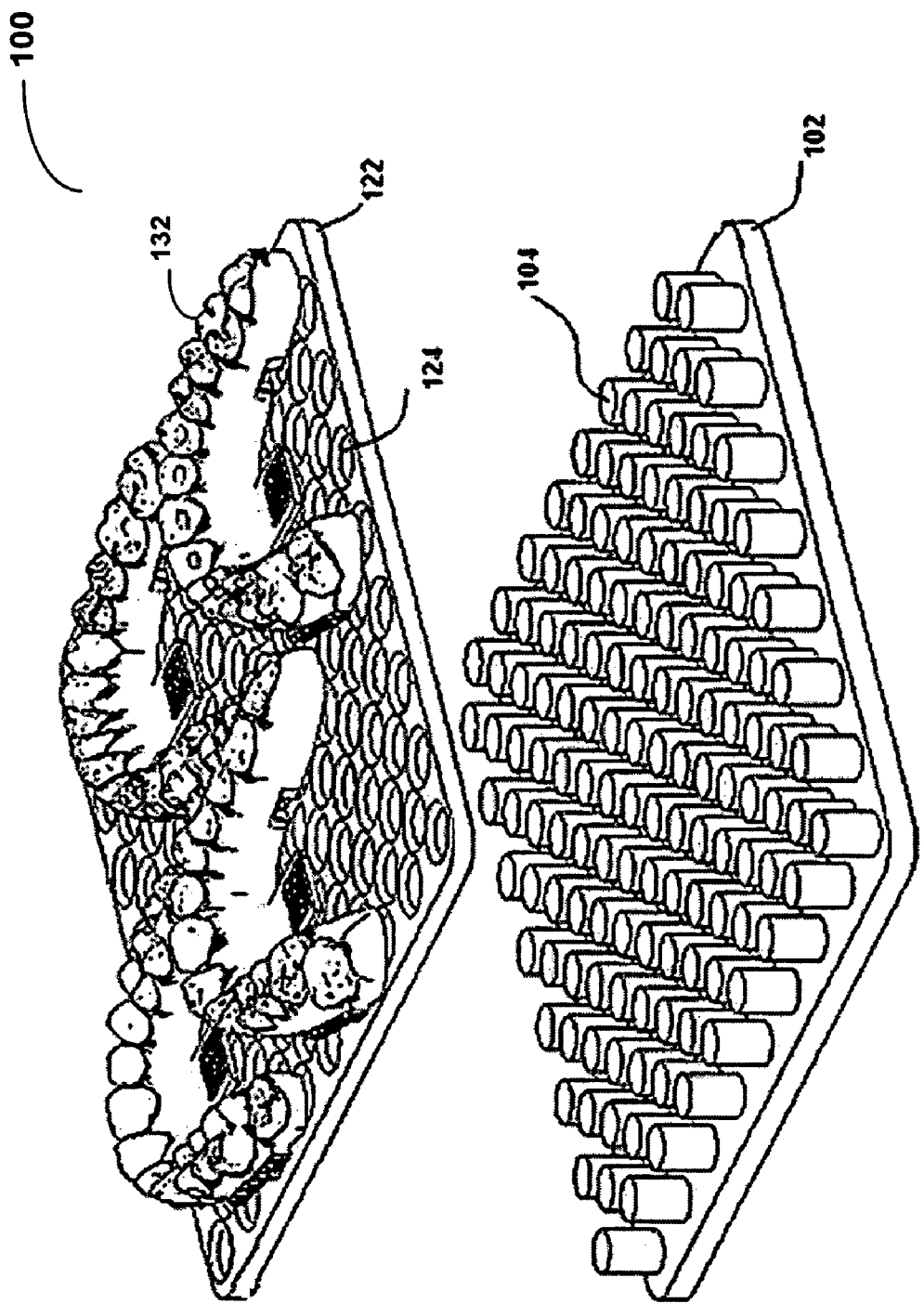
FIGS. 1A-1B are isometric views of one embodiment of a fabrication apparatus.

Referring to FIG. 1A, a platform-punch apparatus is disclosed at 100. The apparatus 100 has a platform 122 that supports the formation of one or more objects 132. The platform 122 includes a plurality of circular openings 124 covering the surface of the apparatus which is adapted to cooperate with the vertical projections 104 of a pinch 102.

Figure 1B:
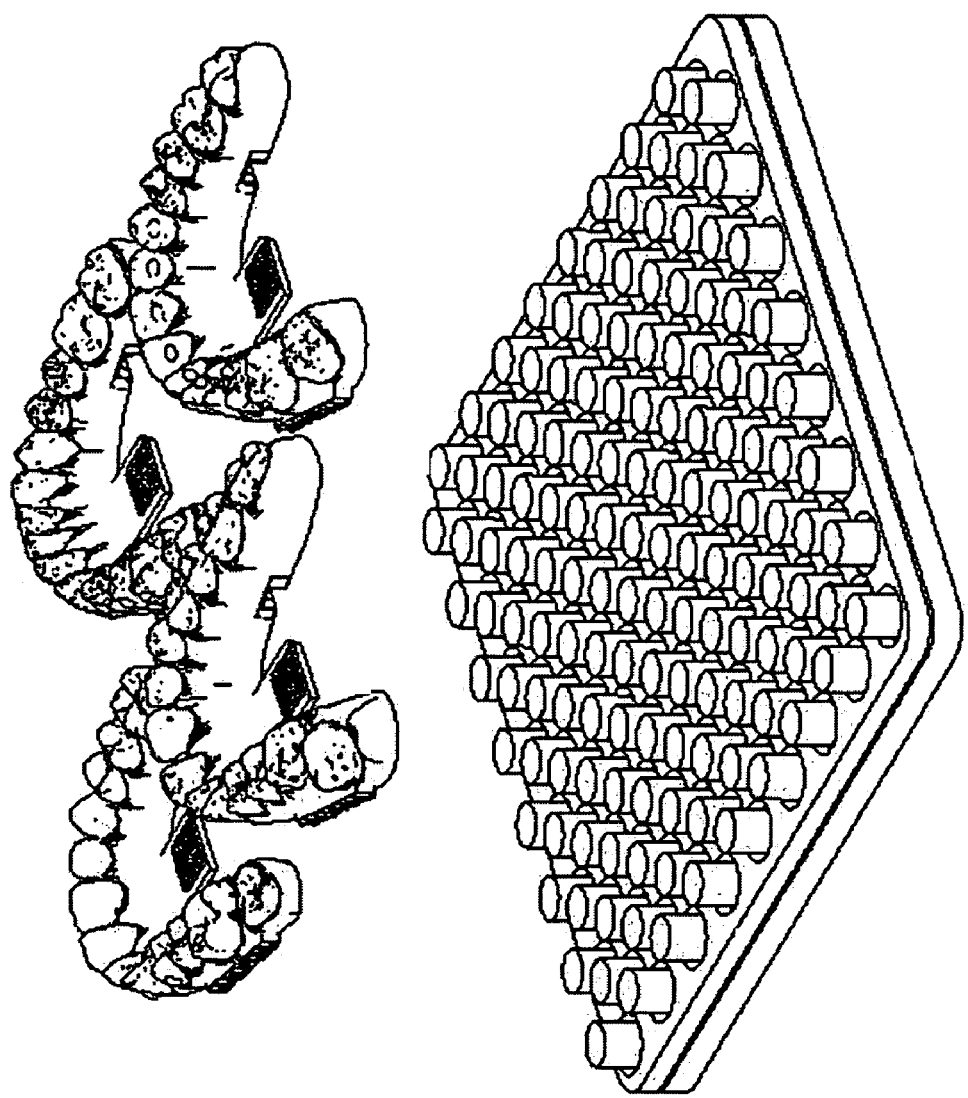

During formation of the object 132, with the platform 122 positioned just below the surface of the photopolymer, a scanning system is used to draw the first cross section on the surface of the photopolymer, which adheres to the apparatus. When the layer is complete, an elevator assembly lowers the platform 122 into a vat and the next layer is drawn, with each new layer adhering to the previous one. The process repeats itself until the object is completed. After the article has formed, the punch 102 having a plurality of projections 104 engages openings 124 in the platform 122 to eject the article from the platform. Alternatively, instead of the punch 102, a tool 714 (see FIGS. 3A-3C) can be used to push the article from the platform. A perspective view of the assembly of the platform 122 and the punch 102 is shown in FIG. 1B. When assembled, the punch 102 ejects the object 132 from the platform 122.

In the embodiment of FIG. 1A, pins 104 are arranged in a grid array and project from the base of the punch. The pins 104 in the grid array are designed to receive corresponding openings 124 on the platform or board 122. The depth and configuration of the pins 104 depend upon the thickness of the platform 122 and the desired height from which a 3D object is to be spaced apart from the top of the platform 122 during manufacturing. In one embodiment, the punch 102 and the platform 122 are substantially square in shape. However, the portions 102 and 122 may be any other suitable shape, including rectangular and circular, among others.

Although the embodiment of FIG. 1A has a plurality of cylindrical pins 104 projecting from the base, any other suitable projections can be used. For example, the punch can include a fin type base having a series of parallel, extending fins, pins or projections 104.

The platform 122 can be made from Teflon in one embodiment. The "Teflon" coatings can be XYLAN® 1840/424 "Pine Green" or XYLON® 8330H 765 "Dark Brown", or any suitable Teflon materials. The substrate material for the apparatus punch 102 can be 303 Stainless Steel, 304 Stainless Steel, or 6061 Aluminum. In another embodiment, the material for a plastic punch such as a removal tool 714 (FIG. 3A) is Delrin, but any rigid plastic would suffice. In another embodiment, the SLA material used to fabricate the SLA molds/tools can be epoxy-based resin containing a "reactive diluent", available from 3D Systems, among others.

In embodiments where the platform is uncoated, materials for the platform can include High Density Poly-Ethylene (HDPE), High Molecular Weight Poly-Ethylene (HMWPE), Ultra High Density Poly-Ethylene (UHDPE), Ultra High Molecular Weight Poly-Ethylene (UHMWPE). The uncoated apparatus materials can have Heat Stabilizer(s) or UV Stabilizer(s).

In embodiments where the platform is coated, materials for the platform of the apparatus can include Aluminum Alloys, Stainless Steels, and High Strength Alloys. The apparatus coating(s) can include Fluorinated Ethylene-Propylene (FEP) under tradenames Teflon or Xylon, among others. The coating can also be Polytetrafluoroethylene (PTFE) under tradenames Teflon or Xylon, among others. The coating can also be silicone(s) such as Wearlon, among others. Other Surface Enhancement Coatings from General Magnaplate can be used, including Tufram, Nedox, Magnaplate HCR, Magnaplate HTR, Magnaplate HMF, Lectrofluor, Hi-T-Lube, Magnagold, and Goldenedge, among others.

Although the punch embodiment shown in FIGS. 1A-1B has pins positioned in a grid array, the pins can be positioned in a random, non-arrayed layout. Other punch shapes can be used as well.

Figure 2A:
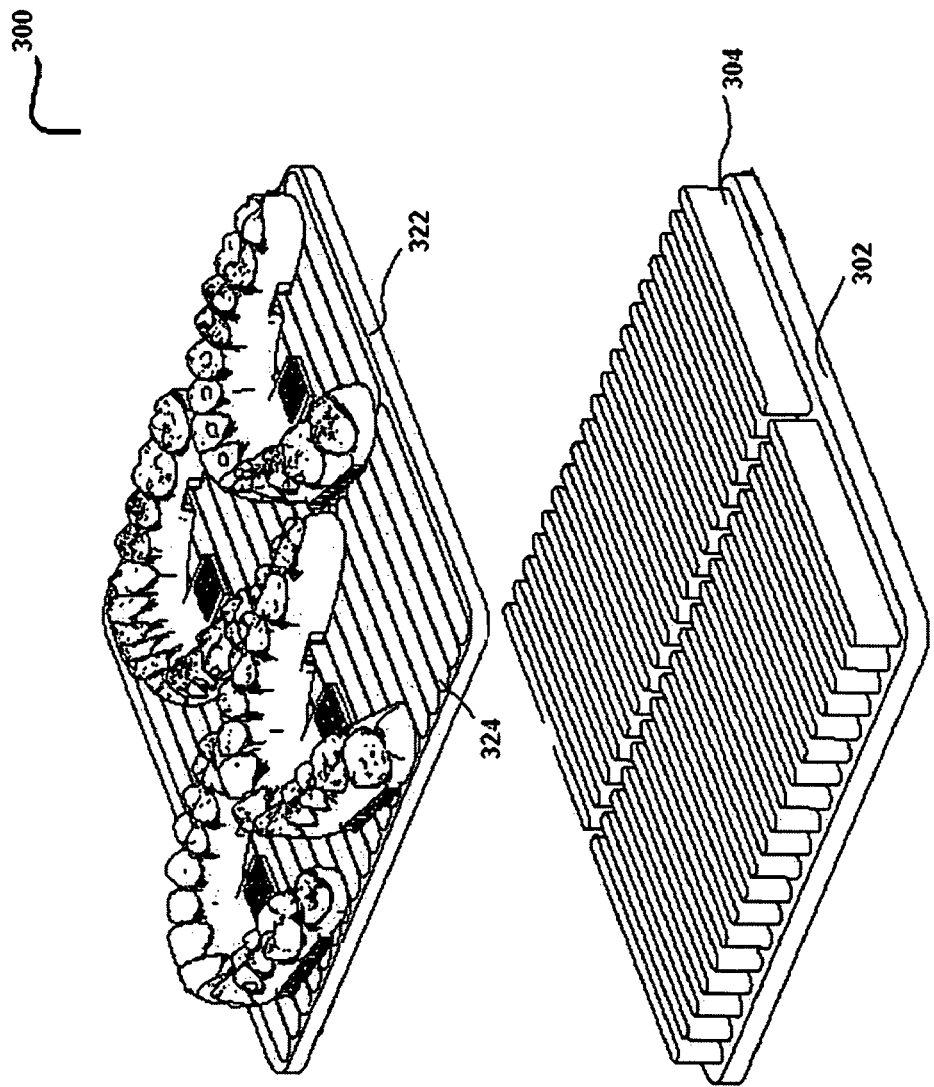
FIGS. 2A-2B are isometric views of a second embodiment of a fabrication apparatus.
Figure 2B:
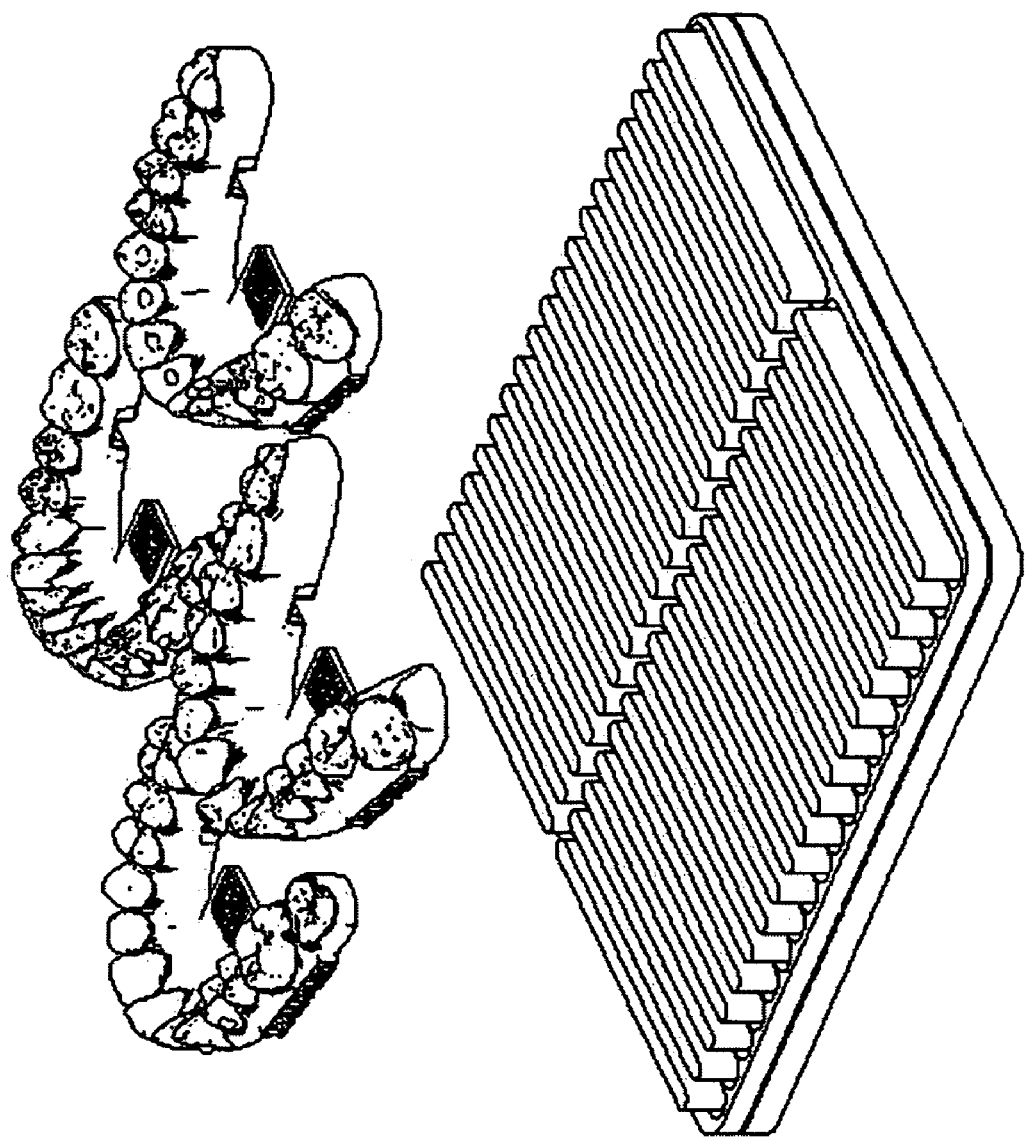

FIG. 2A shows a second embodiment where each opening on a platform has an elongated shape, while FIG. 2B shows an engagement of the platform with a corresponding punch. In FIG. 2A, a platform 322 includes a plurality of elongated horizontal openings or slots 324 which mate or interconnect with corresponding horizontal projections 304 of a mating punch 302. A solid three-dimensional article or object can be formed above the platform 322. The platform of FIG. 2A has two columns of elongated projections 304 that project from the base of the punch 302. The elongated projections 304 in the array of columns are adapted to engage corresponding slots 324 on the platform or board 322 to facilitate removal of objects formed on the platform 322. Again, although the embodiment of FIG. 2A has slots positioned in a columnar array, the slots can be positioned in a random, non-arrayed layout. It should be understood, however, that this arrangement is shown for illustration only, and other layouts may be used.

Figure 3A:
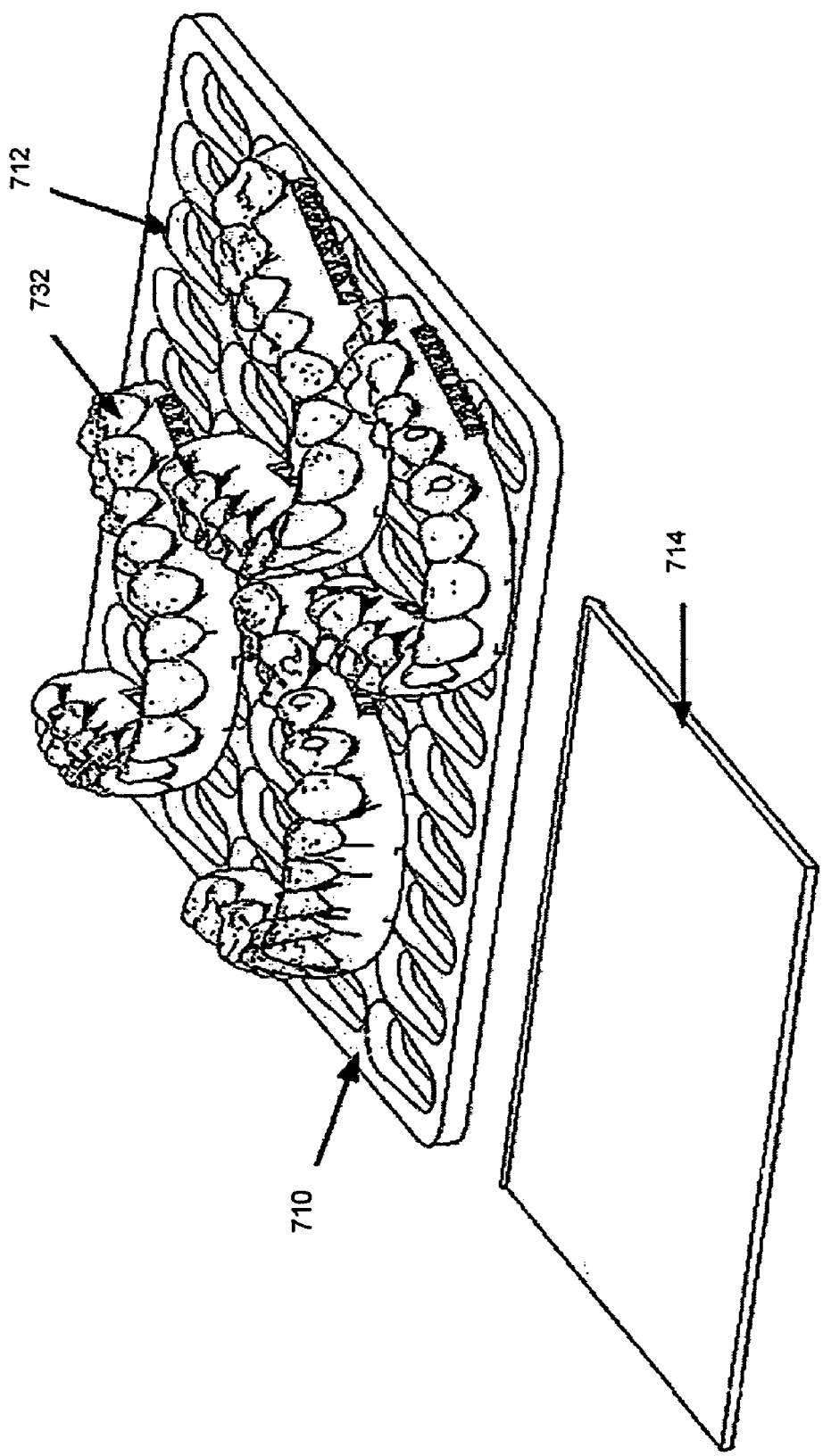
FIGS. 3A-3C are isometric views of a third embodiment of a fabrication apparatus.

FIG. 3A shows a third embodiment where a platform 710 includes a plurality of tear-shaped openings 712. The platform 710 supports the formation of objects 732 formed on the surface of the platform 710. During formation of the object 732, with the platform 710 positioned just below the surface of the photopolymer in a vat, a scanning system is used to draw the first cross section on the surface of the photopolymer, which adheres to the apparatus. When the layer is complete, an elevator assembly lowers the platform 710 into the vat and the next layer is drawn, with each new layer adhering to the previous one. The process repeats itself until the object is completed. After the article has formed, a tool 714 can be used to push the article or object 732 from the platform.

Figure 3B:
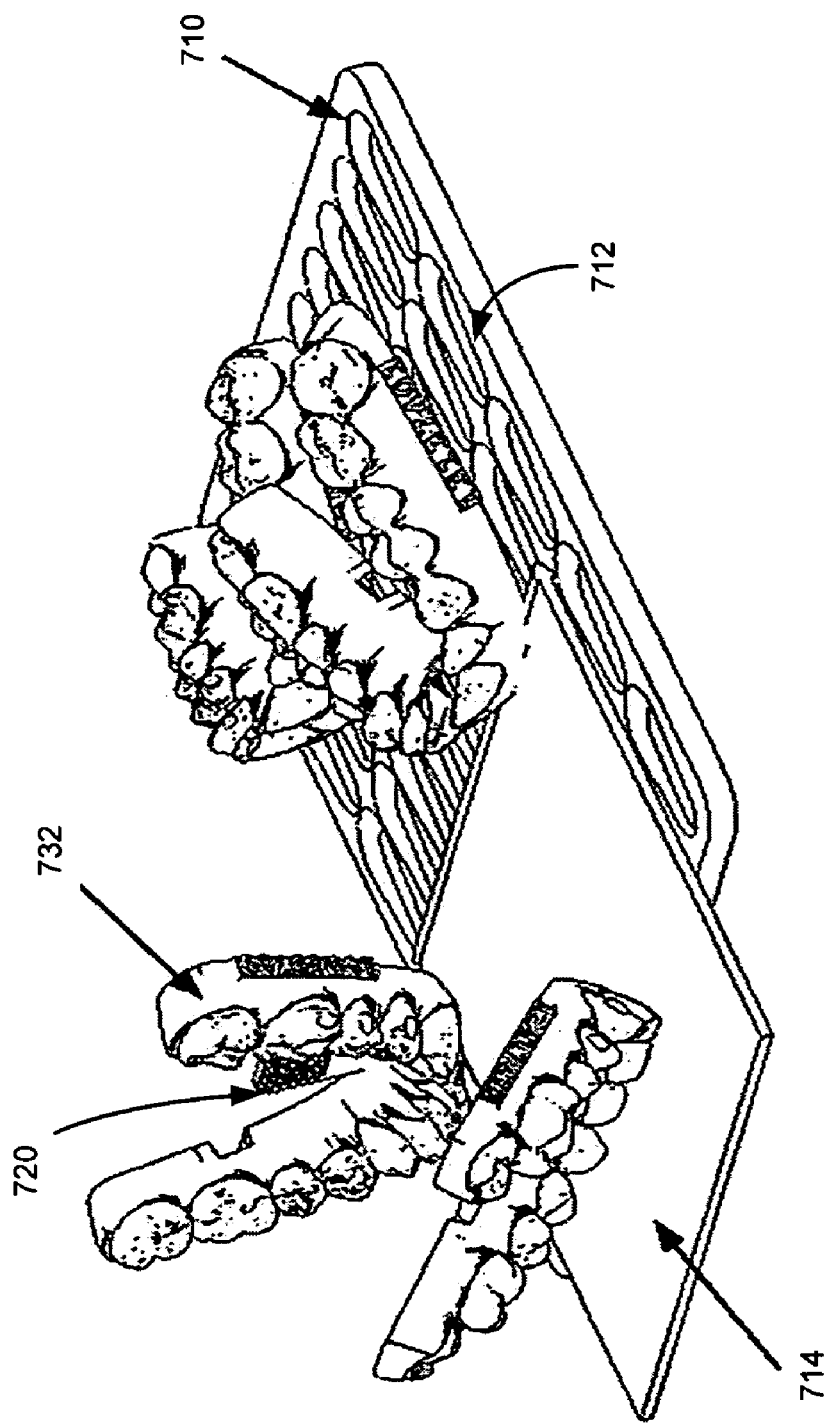
Figure 3C:
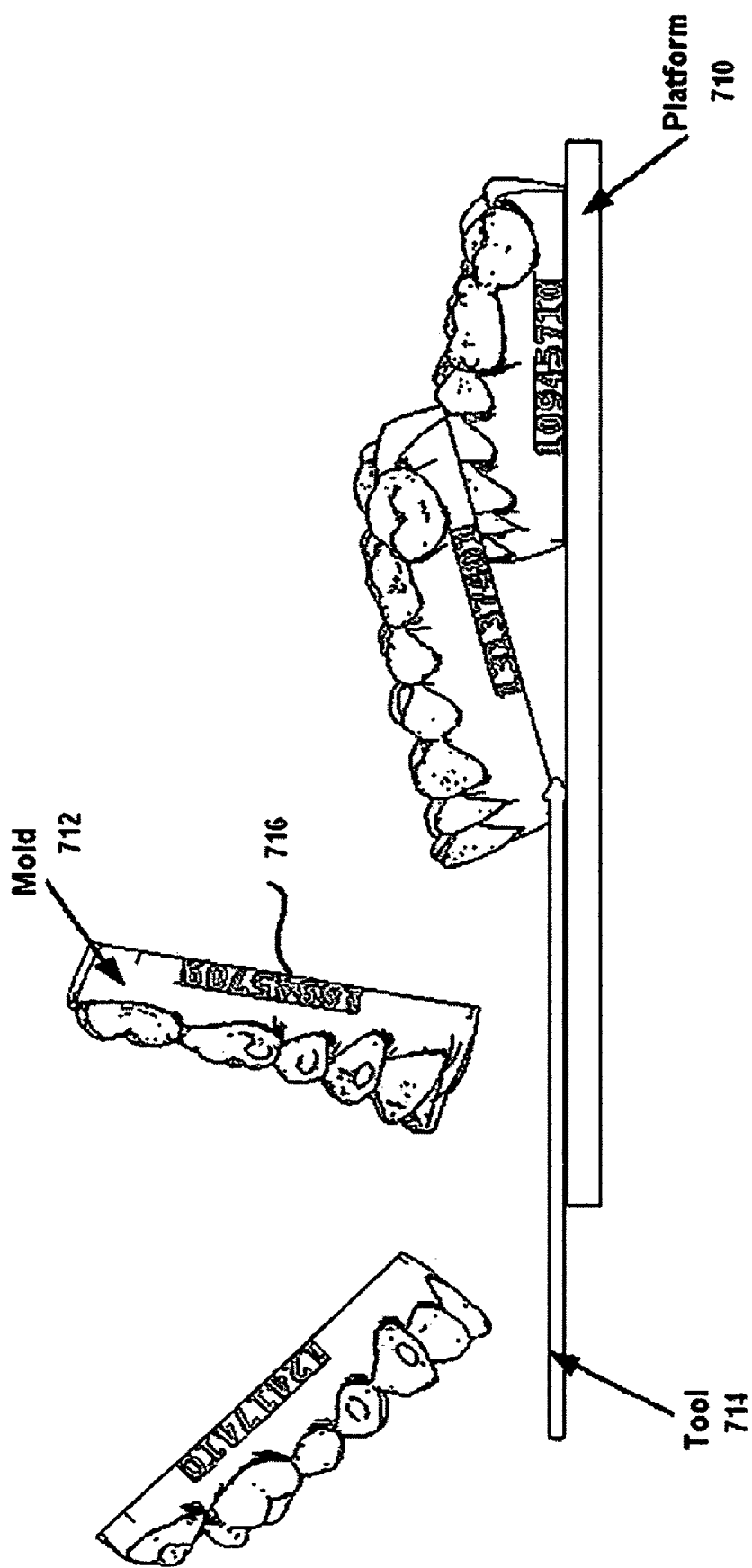

FIGS. 3B and 3C illustrate an exemplary removal process for the 3D article, object or structure. As shown in FIG. 3B, the platform 710 made in accordance with the disclosed structure is used to fabricate a plurality of molds 732. In FIG. 3B, the mold 732 has a machine readable identifier 720, in this case a 2D bar-code imprinted thereon. After fabrication, a tool 714 is used to gently and quickly separate the molds 732 from the apparatus 710. FIG. 3C shows a side view of the mold separation process. As shown in FIG. 3D, an identifier 720 is formed on the mold 732 to facilitate subsequent manufacturing operations.

Figure 4:
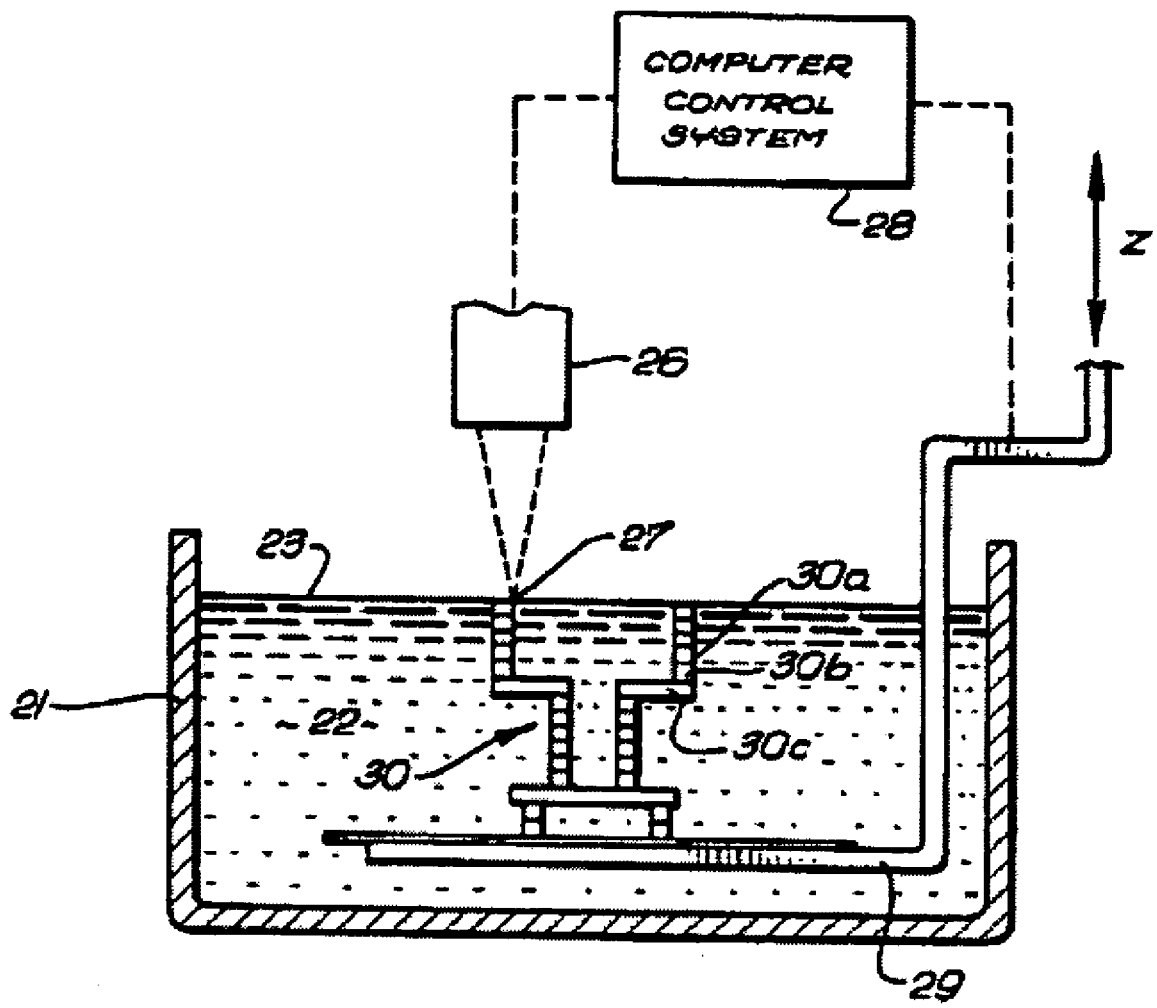
FIG. 4 is an exemplary 3D fabrication machine.

FIG. 4 shows a cross-section or profile of the initial liquid medium layer, in accordance with a design of the solid three-dimensional article being formed, that is solidified using stereo-lithographic technology applying laser beam energy to the liquid medium layer 22 under the direction of a computer. The article is then expeditiously dislodged from the support apparatus once the male and female panels are separated.

With the above described platforms positioned just below the surface of the photopolymer, a scanning system is used to draw the first cross section on the surface of the photopolymer, which adheres to the platform.

When the layer is complete, the elevator assembly lowers the platform into the vat and the next layer is drawn, with each new layer adhering to the previous one. The process repeats itself until the object is completed. Actual build times can range from under an hour to over a day, depending on the photopolymer, laser power, and the object geometry. Typically, a mechanical blade is used to sweep the surface of the photopolymer to ensure an even layer of resin for the next layer. Essentially all types of object forms can be created with the technique of the present invention. Complex forms are more easily created by using the functions of a computer to help generate the programmed commands and to then send the program signals to the stereolithographic object forming subsystem, as discussed in U.S. Pat. No. 4,575,330, the content of which is incorporated by reference.

As shown in elevational cross-section in FIG. 4, a container 21 is filled with a UV curable liquid 22 or the like, to provide a designated working surface 23. A programmable source of ultraviolet light 26 or the like produces a spot of ultraviolet light 27 in the plane of surface 23. The spot 27 is movable across the surface 23 by the motion of mirrors or other optical or mechanical elements (not shown) that are a part of light source 26. The position of the spot 27 on surface 23 is controlled by a computer or other programming device 28. A movable elevator apparatus 29 inside container 21 can be moved up and down selectively, the position of the apparatus being controlled by the computer 28. As the device operates, it produces a three-dimensional object 30 by step-wise buildup of integrated laminae such as 30a, 30b, 30c.

The surface of the UV curable liquid 22 is maintained at a constant level in the container 21, and the spot of UV light 27, or other suitable form of reactive stimulation, of sufficient intensity to cure the liquid and convert it to a solid material is moved across the working surface 23 in a programmed manner. As the liquid 22 cures and solid material forms, the elevator apparatus 29 that was initially just below surface 23 is moved down from the surface in a programmed manner by any suitable actuator. In this way, the solid material that was initially formed is taken below surface 23 and new liquid 22 flows across the surface 23. A portion of this new liquid is, in turn, converted to solid material by the programmed UV light spot 27, and the new material adhesively connects to the material below it. This process is continued until the entire three-dimensional object 30 is formed. The object 30 is then removed from the container 21, and the apparatus is ready to produce another object. Another object can then be produced, or some new object can be made by changing the program in the computer 28.

The curable liquid 22, e.g., UV curable liquid, must have several important properties. (A) It must cure fast enough with the available UV light source to allow practical object formation times. (B) It must be adhesive, so that successive layers will adhere to each other. (C) Its viscosity must be low enough so that fresh liquid material will quickly flow across the surface when the elevator moves the object. (D) It should absorb UV so that the film formed will be reasonably thin. (E) It must be reasonably soluble in some solvent in the liquid state, and reasonably insoluble in that same solvent in the solid state, so that the object can be washed free of the UV cure liquid and partially cured liquid after the object has been formed. (F) It should be as non-toxic and non-irritating as possible.

The cured material must also have desirable properties once it is in the solid state. These properties depend on the application involved, as in the conventional use of other plastic materials. Such parameters as color, texture, strength, electrical properties, flammability, and flexibility are among the properties to be considered. In addition, the cost of the material will be important in many cases.

The UV curable material used in the presently preferred embodiment of a working stereolithograph is a suitable compound available from 3D Systems, Inc., among others. A process to make a typical UV curable material is described in U.S. Pat. No. 4,100,141 entitled Stabilized Adhesive and Curing Compositions, the content of which is incorporated by reference.

The light source 26 produces the spot 27 of UV light small enough to allow the desired object detail to be formed, and intense enough to cure the UV curable liquid being used quickly enough to be practical. The source 26 is arranged so it can be programmed to be turned off and on, and to move, such that the focused spot 27 moves across the surface 23 of the liquid 22. Thus, as the spot 27 moves, it cures the liquid 22 into a solid, and "draws" a solid pattern on the surface in much the same way a chart recorder or plotter uses a pen to draw a pattern on paper.

The light source 26 for the presently preferred embodiment of a stereolithograph is made using a 350 watt mercury short arc lamp in a housing, with the light output of the housing focused on the end of a 1 mm diameter UV transmitting fiber optic bundle (not shown). The end of the bundle next to the lamp is water cooled, and there is an electronically controlled shutter blade between the lamp and the end of the bundle, which can turn the light through the bundle on and off. The bundle is 1 meter long, and the optical output is fitted into a lens tube that has a quartz to focus the UV to a spot. The light source 26 is capable of producing a spot somewhat less than 1 mm in diameter, with a long wave UV intensity of about 1 watt/cm2.

In the system of FIG. 4, means may be provided to keep the surface 23 at a constant level and to replenish this material after an object has been removed, so that the focus spot 27 will remain sharply in focus on a fixed focus plane, thus insuring maximum resolution in forming a thin layer along the working surface. In this regard, it is desired to shape the focal point to provide a region of high intensity right at the working surface 23, rapidly diverging to low intensity and thereby limiting the depth of the curing process to provide the thinnest appropriate cross-sectional laminae for the object being formed. This is best accomplished by using a short focal length lens and bringing the source 26 as close as possible to the working surface, so that maximum divergence occurs in the cone of focus entering the fluid medium. The result is substantially enhanced resolution.

Other physical forms of the light source 26 or its equivalent are feasible. Scanning could be done with optical scanners, and this would eliminate the fiber optic bundle and the digital plotter. A UV laser might ultimately be a better light source than a short arc lamp. The speed of the stereolithographic process is mainly limited by the intensity of the light source and the response of the UV curable liquid.

The elevator apparatus 29 is used to support and hold the object 30 being formed, and to move it up and down as required. Typically, after a layer is formed, the object 30 is moved beyond the level of the next layer to allow the liquid 22 to flow into the momentary void at surface 23 left where the solid was formed, and then it is moved back to the correct level for the next layer. The requirements for the elevator apparatus 29 are that it can be moved in a programmed fashion at appropriate speeds, with adequate precision, and that it is powerful enough to handle the weight of the object 30 being formed. In addition, a manual fine adjustment of the elevator apparatus position is useful during the set-up phase and when the object is being removed.

The elevator apparatus 29 for the embodiment of FIG. 4 is an apparatus attached to one or more motors driven by digital to analog converters under program control of the computer 28. The computer 28 in the stereolithographic system has two basic functions. The first is to help the operator design the three-dimensional object in a way that it can be made. The second is to translate the design into commands that are appropriate for the other stereolithographic components, and to deliver these commands in a way so that the object is formed. In some applications, the object design will exist, and the only function of the computer will be to deliver the appropriate commands.

In an ideal situation, the operator will be able to design the object and view it three-dimensionally on the CRT screen of the computer 28. When he is finished with the design, he will instruct the computer 28 to make the object, and the computer will issue the appropriate instructions to the stereolithographic components.

The elevator apparatus 29 can be mechanical, pneumatic, hydraulic, or electrical and may also use optical or electronic feedback to precisely control its position. In some cases, the computer 28 becomes unnecessary and simpler dedicated programming devices can be used, particularly where only simply shaped objects are to be formed. Alternatively, the computer control system 28 can be simply executing instructions that were generated by another, more complex, computer. This might be the case where several stereolithography units are used to produce objects, and another device is used to initially design the objects to be formed.

A computer controlled pump (not shown) may be used to maintain a constant level of the liquid 22 at the working surface 23. Appropriate level detection system and feedback networks, well known in the art, can be used to drive a fluid pump or a liquid displacement device, such as a solid rod (not shown) which is moved out of the fluid medium as the elevator apparatus is moved further into the fluid medium, to offset changes in fluid volume and maintain constant fluid level at the surface 23. Alternatively, the source 26 can be moved relative to the sensed level 23 and automatically maintain sharp focus at the working surface 23. All of these alternatives can be readily achieved by conventional software operating in conjunction with the computer control system 28.

After the three-dimensional object 30 has been formed, the elevator apparatus 29 is raised and the object is removed from the apparatus. Typically, the object is then ultrasonically rinsed in a solvent, such as acetone, that dissolves the liquid state of the uncured fluid medium and not the cured solid state medium. The object 30 is then placed under an intense ultraviolet floodlight, typically a 200 watt per inch UV cure lamp, to complete the curing process.

In one embodiment, the 3D structure is a dental model such as a dental cast.

Figure 5:
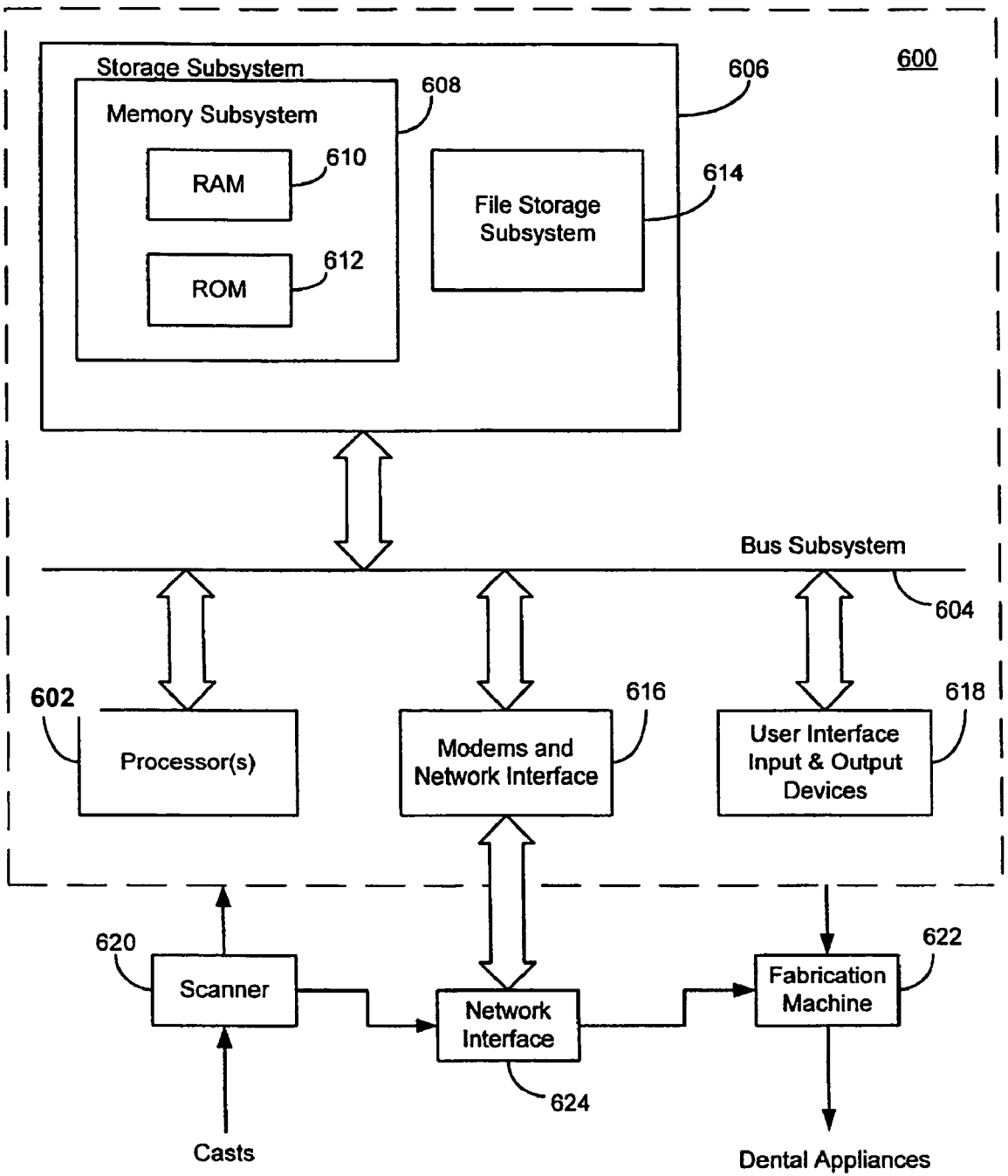
FIG. 5 is a simplified block diagram of a data processing system that may be used to control the 3D fabrication machine of FIG. 4 to generate a 3D structure such as a dental model or a dental appliance.

FIG. 5 is a simplified block diagram of a data processing system 600 that may be used to generate a 3D structure such as a dental model or a dental appliance directly. The data processing system 600 typically includes at least one processor 602 that communicates with a number of peripheral devices via bus subsystem 604. These peripheral devices typically include a storage subsystem 606 (memory subsystem 608 and file storage subsystem 614), a set of user interface input and output devices 618, and an interface to outside networks 616, including the public switched telephone network. This interface is shown schematically as "Modems and Network Interface" block 616, and is coupled to corresponding interface devices in other data processing systems via communication network interface 624. Data processing system 600 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touch screen incorporated into the display, or a three dimensional pointing device, such as the gyroscopic pointing device described in U.S. Pat. No. 5,440,326. Other types of user interface input devices, such as voice recognition systems, can also be used. User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 606 maintains the basic required programming and data constructs. The program modules discussed above are typically stored in storage subsystem 606. Storage subsystem 606 typically comprises memory subsystem 608 and file storage subsystem 614.

Memory subsystem 608 typically includes a number of memories including a main random access memory (RAM) 610 for storage of instructions and data during program execution and a read only memory (ROM) 612 in which fixed instructions are stored. In the case of Macintosh-compatible personal computers the ROM would include portions of the operating system; in the case of IBM-compatible personal computers, this would include the BIOS (basic input/output system). File storage subsystem 614 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by SyQuest and others, and flexible disk cartridges, such as those marketed by Iomega. One or more of the drives may be located at a remote location, such as in a server on a local area network or at a site on the Internet's World Wide Web. In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used. Bus subsystem 604 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 620 is responsible for scanning casts of the patient's teeth obtained either from the patient or from an orthodontist and providing the scanned digital data set information to data processing system 600 for further processing. In a distributed environment, scanner 620 may be located at a remote location and communicate scanned digital data set information to data processing system 600 via network interface 624. Fabrication machine 622 (such as the fabrication machine of FIG. 4) fabricates dental appliances based on intermediate and final data set information received from data processing system 600. In a distributed environment, fabrication machine 622 may be located at a remote location and receive data set information from data processing system 600 via network interface 624. More information on the fabrication of dental appliances is discussed in U.S. Pat. No. 5,975,893 entitled "Method and system for incrementally moving teeth", the content of which is hereby incorporated by reference.

The information needed to drive the fabrication machine 622 can originate from an intraoral scanner, a destructive scanner, or a non-destructive scanner. In one embodiment, the non-destructive scanner is a CT scanner. In this embodiment, an apparatus to create a digital model of a patient's teeth includes a radiation source; a scintillator to receive the radiation from the radiation source; a radiation detector coupled to the scintillator; a rotatable table positioned between the radiation source and the scintillator, the table being adapted to support an impression of the patient's teeth; and a computer coupled to the detector to generate the digital model with scanned data. A fabrication machine can be driven by the computer to generate a plurality of appliances, wherein the appliances comprise polymeric shells having cavities and wherein the cavities of successive shells have different geometries shaped to receive and resiliently reposition the teeth from one arrangement to a successive arrangement. Such systems are described in U.S. Pat. Nos. 6,633,789; 6,629,840; 6,626,666; 6,621,491; 6,607,382; 6,602,070; 6,582,229; 6,582,227; 6,572,372; 6,554,611; 6,524,101; 6,514,074; 6,499,997; 6,497,574; 6,488,499; 6,485,298; 6,471,511; 6,463,344; 6,457,972; 6,454,565; 6,450,807; 6,409,504; 6,406,292; 6,398,548; 6,394,801; 6,390,812; 6,386,878; 6,386,864; 6,371,761; 6,318,994; 6,309,215; 6,299,440; 6,227,851; 6,227,850; 6,217,325; 6,210,162; 5,975,893, the contents of which are hereby incorporated by reference.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An apparatus for forming articles from successively-deposited and solidified layers of a liquid medium, comprising:
    platform having first and second opposed surfaces, the first surface being configured for the deposition thereon and the adhesion thereto of successive layers of the liquid medium, wherein the first surface comprises a material that adheres to the liquid medium as it solidifies, the adhesion between the first surface and the solidified liquid medium being sufficient to retain the successively-deposited layers on the first surface as each layer is solidified while permitting the removal of the article from the first surface without breakage;
    a plurality of openings in the platform, each of the openings extending through the first and second surfaces of the platform; and
    a punch having a plurality of projections, each configured to engage one of the openings in the platform, the punch being operable to insert the projections into the openings from the second surface of the platform so as to remove from the platform the articles formed on the first surface.

2. The apparatus of claim 1, wherein the openings comprise a regular array.

3. The apparatus of claim 1, wherein the openings are formed in an irregular pattern.

4. The apparatus of claim 1, wherein each opening is circular shaped or oval shaped.

5. The apparatus of claim 1, wherein each opening is rectangular shaped.

6. The apparatus of claim 1, wherein each opening is teardrop shaped.

7. The apparatus of claim 1, wherein each opening is elongated.

8. The apparatus of claim 1, wherein the openings are positioned in one or more columns.

9. The apparatus of claim 1, wherein the platform comprises a coating material on the first surface that adheres to the solidified liquid medium.

10. Apparatus for use in a rapid prototyping machine, of the type that forms a three-dimensional article from successively-deposited layers of a liquid photopolymer medium that is solidified by the application thereto of radiation energy, the apparatus further being of the type including container containing the liquid photopolymer medium, the apparatus comprising:
    a platform configured and operable for vertical translation within the container and having first and second oppose surfaces defining a surface area, the first surface being configured for the deposition thereon and the adhesion thereto of successive layers of the liquid photopolymer medium, wherein the first surface comprises a material that adheres to the liquid photopolymer medium as it solidifies, the adhesion between the first surface and the solidified photopolymer medium being sufficient to retain the successively-deposited layers on the first surface as each layer is solidified in forming the article, while permitting the removal of the article from the first surface without breakage; and
    an array of openings occupying most of the surface area of the platform, each of the openings extending through the first and second surfaces of the platform, the openings being configured and arranged to minimize the contact area between the first surface of the platform and the solidified photopolymer, thereby to facilitate the removal of the article from the first surface of the platform.

11. The apparatus of claim 10, further comprising a removal device for removing the article from the first surface of the platform by breaking the adhesion between the first surface and the solidified liquid photopolymer medium deposited thereon.

12. The apparatus of claim 11, wherein the removal device comprises a punch having a plurality of projections, each of which is configured to engage one of the openings in the platform, the punch being operable to insert the projections into the openings from the second surface of the platform so as to remove the article the first surface.

13. The apparatus of claim 10, wherein the opening: in the array of openings are configured to permit the passage therethrough of the liquid photopolymer medium from the second surface to the first surface of the platform as the platform is translated vertically within the container.

14. The apparatus of claim 10, wherein the article is one of a plurality of unique articles formed on the platform, wherein the platform is configured for the formation of the plurality of articles on the first surface thereof, and wherein the openings are configured and arranged to minimize the contact area between the first surface of the platform and the solidified photopolymer forming the plurality of articles, thereby to facilitate the removal of the plurality of articles from the first surface of the platform.

15. The apparatus of claim 10, wherein the platform comprises a material selected from the group consisting of at least one of High Density Poly-Ethylene (HDPE), High Molecular Weight Poly-Ethylene (HMWPE), Ultra High Density Poly-Ethylene (UHDPE), and Ultra High Molecular Weight Poly-Ethylene UHMWPE).

16. The apparatus of claim 15, wherein the platform material further comprises at least one of a heat stabilizer and a UV stabilizer.

17. The apparatus of claim 10, further comprising a coating on the first surface of the platform, wherein the coating comprises a material that adheres to the solidified photopolymer medium.

18. The apparatus of claim 17, wherein the platform comprises a material selected from the group consisting of Aluminum Alloys, Stainless Steels, or High Strength Alloys.

19. The apparatus of claim 17, wherein the coating comprises a material selected from the group consisting of Fluorinated Ethylene-Propylene (FEP), Polytetrafluoroethylene (PTFE), and silicone.

* * * * *

UNITED STATES PATENT AND TRADEMARK OFFICE
CERTIFICATE OF CORRECTION

PATENT NO.        : 7,481,647 B2
APPLICATION NO.   : 10/867099
DATED             : January 27, 2009
INVENTOR(S)       : Shiva P. Sambu et al.

It is certified that error appears in the above-identified patent and that said Letters Patent is hereby corrected as shown below:

In column 2, line 59, delete "pinch" and insert -- punch --, therefor.

In column 6, line 9, delete "watt/cm2." and insert -- watt/cm$^2$. --, therefor.

In column 9, line 52, in Claim 1, before "platform" insert -- a --.

In column 10, line 24, in Claim 10, after "including" insert -- a --.

In column 10, line 28, in Claim 10, delete "oppose" and insert -- opposed --, therefor.

In column 10, line 58, in Claim 12, after "article" and insert -- from --.

In column 10, line 59, in Claim 13, delete "opening:" and insert -- openings --, therefor.

In column 11, line 11, in Claim 15, delete "UHMWPE)." and insert -- (UHMWPE). --, therefor.

Signed and Sealed this

Eighth Day of December, 2009

David J. Kappos
*Director of the United States Patent and Trademark Office*